United States Patent
Cho et al.

(10) Patent No.: US 7,405,070 B2
(45) Date of Patent: Jul. 29, 2008

(54) METHOD FOR PREPARING (S)-INDOLINE-2-CARBOXYLIC ACID AND (S)-INDOLINE-2-CARBOXYLIC ACID METHYL ESTER USING HYDROLYTIC ENZYME

(75) Inventors: Nahm Ryune Cho, Daejeon (KR); Jong Ho Lim, Daejeon (KR); Jong Keun Kim, Daejeon (KR)

(73) Assignee: SK Corporation, Seoul (KR)

( * ) Notice: Subject to any disclaimer, the term of this patent is extended or adjusted under 35 U.S.C. 154(b) by 273 days.

(21) Appl. No.: 10/596,068

(22) PCT Filed: Nov. 3, 2004

(86) PCT No.: PCT/KR2004/002806

§ 371 (c)(1), (2), (4) Date: May 26, 2006

(87) PCT Pub. No.: WO2005/051910

PCT Pub. Date: Jun. 9, 2005

(65) Prior Publication Data

US 2007/0077632 A1    Apr. 5, 2007

(30) Foreign Application Priority Data

Nov. 26, 2003 (KR) .................. 10-2003-0084492

(51) Int. Cl.
- C12P 41/00 (2006.01)
- C12P 17/10 (2006.01)
- C12N 9/12 (2006.01)
- C12N 9/14 (2006.01)
- C12N 9/16 (2006.01)

(52) U.S. Cl. .................. 435/280; 435/121; 435/195; 435/196; 435/197

(58) Field of Classification Search .................. 435/121
See application file for complete search history.

(56) References Cited

U.S. PATENT DOCUMENTS

| 4,614,806 A | 9/1986 | Buzby, Jr. et al. |
| 4,898,822 A | 2/1990 | Asada et al. |

FOREIGN PATENT DOCUMENTS

| DE | 3727411 | 3/1998 |
| EP | 0197474 | 10/1986 |
| EP | 0 937 714 | 6/2004 |
| JP | 61-92595 | 6/1986 |
| JP | 06-16718 | 1/1994 |
| JP | 07-79711 | 3/1995 |
| JP | 07-79712 | 3/1995 |

OTHER PUBLICATIONS

M.Vincent et al., Tetrahedron Letters, vol. 23, No. 16, pp. 1677-1680, 1982.
Ryoichi Kuwano et al., J. Am. Chem. Soc. 2000, 122, 7614-7615.
Mahmoud Mahmoudian, et al. A practical enzymatic procedure for the resolution of N-substituted 2-azabicyclo[2.2.1]hept-5-en-3-one 10 (1999) 1201-1206.

*Primary Examiner*—Herbert J Lilling
(74) *Attorney, Agent, or Firm*—Darby & Darby P.C.

(57) ABSTRACT

Disclosed is a method for preparing (S)-indoline-2-carboxylic acid and (S)-indoline-2-carboxylic acid methyl ester using an inexpensive industrially available enzyme capable of assuring superior optical purity and yield. At this time, the hydrolytic enzyme is selected from the group consisting of Savinase, Alcalase, Novozym 243, Everlase, Esperase, Protease 7 and Acylase, whereby (S)-indoline-2-carboxylic acid and methyl ester thereof having an optical purity of at least 99% e.e. can be obtained through a simplified preparation process, thus generating economic benefits.

14 Claims, No Drawings

METHOD FOR PREPARING (S)-INDOLINE-2-CARBOXYLIC ACID AND (S)-INDOLINE-2-CARBOXYLIC ACID METHYL ESTER USING HYDROLYTIC ENZYME

CROSS REFERENCE TO PRIOR APPLICATIONS

This application is a U.S. national phase application under 35 U.S.C. §371 of International Application No. PCT/KR2004/002806, filed Nov. 3, 2004, and claims the benefit of Korean Application No. 10-2003-0084482, filed Nov. 26, 2003, both of which are incorporated by reference herein. The International Application was published in English on Jun. 9, 2005 as International Publication No. WO/2005/051910 under PCT Article 21(2).

TECHNICAL FIELD

The present invention relates, in general, to the preparation methods of (S)-indoline-2-carboxylic acid and methyl ester thereof using hydrolytic enzymes. More specifically, the present invention pertains to a method for preparing (S)-indoline-2-carboxylic acid and (S)-indoline-2-carboxylic acid methyl ester having an optical purity of at least 99% e.e., from racemic indoline-2-carboxylic acid methyl ester, by use of an industrially available hydrolytic enzyme, derived from microorganisms.

BACKGROUND ARTS

In general, (S)-indoline-2-carboxylic acid and methyl ester compounds thereof are currently used as an intermediate of many novel medicines in experimental and clinic steps, and as well, may be applied as an intermediate of a therapeutic agent for the treatment of hypertension, such as Perindopril™, which is presently commercially available from Servier (France), when being converted to (2S)-(2α,3αβ, 7αβ)-octahydroindole-2-carboxylic acid through hydrogenation. Thus, intensive researches on (S)-indoline-2-carboxylic acid and (S)-indoline-2-carboxylic acid methyl ester have been performed.

At present, the production of optically active (S)-indoline-2-carboxylic acid and methyl ester thereof is largely classified into four methods, that is, (1) recrystallization using a chiral auxiliary, (2) asymmetrical hydrogenation using a chiral auxiliary, (3) chemical synthesis through asymmetrical reduction using a chiral auxiliary, and (4) enantioselective hydrolysis using a microorganism and an enzyme.

First, the recrystallization method is characterized in that an optically active compound is used as an auxiliary, and thus a certain optical isomer is selectively pre-cipitated as a salt and separated from the other optical isomer. In this regard, (+)-alpha-methylbenzylamine is used as the chiral auxiliary to separate only (S)-indoline-2-carboxylic acid having optical purity of 96% e.e. (Vincent M. et al., Tetrahedron Letters, 23(16), 1677, 1982).

In addition, $(-)$-$(R,R)$-4-$(O_2N)C_6H_4CH(OH)CH(NH_2)CH_2OH$ is utilized as the chiral auxiliary, along with acetylated indoline-2-carboxylic acid, thereby separating only the acetylated (S)-indoline-2-carboxylic acid with an optical purity of 99% e.e. (Hendrickx A. J. J. & Kuilman T., EP 937,714 (1999)). However, the recrystallization method is disadvantageous in that the used chiral auxiliary is expensive and also is difficult to recover, thus negating economic benefits. Thus, it is difficult to apply the above method to commercial industries.

Second, the asymmetrical hydrogenation method using the chiral auxiliary is characterized in that a substrate and a metal catalyst having a chiral ligand are added to a solvent, followed by optically selective hydrogenation of the substrate. For example, acetylated indoline-2-carboxylic acid methyl ester is hydrogenated, together with $[Rh(norbomadiene)2]^+SbF6^-$ as the catalyst, and bis(diphenylphosphinoethyl)-biferrocene (S,S)-(R,R)-PhTRAP as the ligand, in an isopropanol solution containing cesium carbonate, under the conditions of 60° C. and 5.0 Mpa, to produce acetylated (S)-indoline-2-carboxylic acid methyl ester with an optical purity of 95% e.e., as the yield of 95% (Kuwano R. et al., JACS, 122(31), 7614, 2000). The above method is advantageous in terms of high yield of the product, but suffers from drawbacks, such as low optical purity, and the use of expensive chiral auxiliary for the hydrogenation, in which the chiral auxiliary is difficult to synthesize. Further, since the above hydrogenation method requires expensive equipments and facilities, it cannot be employed for a large-scaled process.

Third, the chemical synthesis method through the asymmetrical reduction using the chiral auxiliary is characterized by optically selective reduction of a pro-chiral type nitrophenyl pyruvic acid by use of the chiral auxiliary, to prepare an alcohol derivative, which is then used as an intermediate to produce optically active (S)-indoline-2-carboxylic acid. In this regard, while D-(+)-Proline and sodium borohydride $(NaBH_4)$ are used as the chiral auxiliary and a reducing agent, respectively, nitrophenyl pyruvic acid is subjected to an optically selective reduction, thus synthesizing (S)-alpha-hydroxybenzenepropionic acid with the yield of 85%. Subsequently, the synthesized (S)-alpha-hydroxybenzenepropionic acid is chlorinated, followed by reducing a nitro group to an amine group to make a cyclic structure in a basic aqueous solution, to finally synthesize (S)-indoline-2-carboxylic acid (Buzby G. C. Jr et al., U.S. Pat. No. 4,614,806 (1988)). However, the above method is disadvantageous in that (S)-indoline-2-carboxylic acid is synthesized through many reaction steps, for example, four steps from nitrophenyl pyruvic acid, thus obtaining a very low reaction yield, not more than 32%. Further, the above method is disadvantageous in terms of the use of expensive of D-(+)-proline, and thus it is impossible to produce the target product economically.

Fourth, the enantioselective hydrolysis method using the microorganism and the enzyme includes two type processes proposed separately by Asada et al. and Oreste et al.

By Asada et al., alcohol having a higher molecular weight, selected from the group consisting of butanol, amylalcohol, benzylalcohol, cyclohexanol, cyclohexandiol, glycerol, glycerol-alpha-monochlorohydrine, ethyleneglycol, dichloropropanol, monochlorohydrine, and pentantriol, reacts with racemic indoline-2-carboxylic acid to prepare an ester compound, which is then subjected to an optically selective resolution by use of an industrial enzyme and an enzyme purified from microorganisms, to produce (S)- or (R)-ester compound, which is then further hydrolyzed, concentrated, crystallized, precipitated and filtered, thus finally obtaining (S)- or (R)-indoline-2-carboxylic acid having high optical purity (Asada et al., U.S. Pat. No. 4,898,822 (1990)).

Although the ester compound composed of alcohol having a higher molecular weight, used as the substrate, can increase the yield due to the enhancement of an adsorption ratio to a hydrophobic resin filled in a column, it decreases the number of moles per unit volume in the same amount, compared to ester compounds having a lower molecular weight, thereby lowering the yield of the overall reaction, resulting in increased process costs.

Among the enzymes and microorganisms using by Asada et. al., steapsin and a hydrolytic enzyme derived from *Arthrobacter nicotianea* have relatively higher activity.

Although steapsin is an inexpensive lipase obtained from the pancreas of pigs, it has only 25% of protein based on total amounts thereof, in which the protein further includes amylase and protease. Thereby, side reactions occur and thus impurities are easily produced. Also, upon separation and purification of the product, since an emulsion layer is formed by impurities and unnecessary proteins in the total proteins of Steapsin, the separation/purification process is difficult to perform, and as well, the purification yield decreases.

Moreover, the enzymes derived from the microorganisms are different in titers and activities according to culture conditions of the microorganisms, and the purification of enzymes requires a complicated process, such as column chromatography. Further, the (S)- or (R)-ester compound obtained from the enzymatic reaction can be converted to (S)- or (R)-indoline-2-carboxylic acid having high optical purity by means of complicated processes, such as hydrolysis, concentration, crystallization, pre-cipitation and filtration. Hence, the reaction process suffers from complexity and the lower yield, thus negating economic benefits.

Meanwhile, by Oreste et al., the racemic acetylated indoline-2-carboxylic acid methyl ester is selectively hydrolyzed by the microorganism and the enzyme to produce the acetylated (S)-indoline-2-carboxylic acid methyl ester having optical activity (Oreste G. et al., DE 3,727,411 (1988)). However, since the resultant acetylated (S)-indoline-2-carboxylic acid methyl ester has the yield of 9% and the optical purity of maximal 98% e.e., the above method cannot be applied for an industrial production process requiring both high optical activity and high yield. Further, because the acetyl group should be removed from the product, the chiral center may be easily racemized, therefore decreasing the optical purity.

SUMMARY OF THE INVENTION

Leading to the present invention, the intensive and thorough research on production methods of (S)-indoline-2-carboxylic acid and methyl ester thereof, carried out by the present inventors aiming to avoid the problems encountered in the prior arts, resulted in the finding that methyl alcohol having a lower molecular weight reacts with racemic indoline-2-carboxylic acid to prepare racemic indoline-2-carboxylic acid methyl ester, which is then subjected to optical resolution by use of an industrially available hydrolytic enzyme, whereby (S)-indoline-2-carboxylic acid and ester compounds thereof having high optical purity can be obtained.

Therefore, it is an object of the present invention to provide a method for preparing (S)-indoline-2-carboxylic acid and (S)-indoline-2-carboxylic acid methyl ester using a hydrolytic enzyme, which is advantageous in terms of a simplified preparation process, and high preparation efficiencies.

According to a first aspect of the present invention, there is provided a method for preparing (S)-indoline-2-carboxylic acid methyl ester by use of a hydrolytic enzyme, including the steps of reacting racemic indoline-2-carboxylic acid with methanol and thionyl chloride, to give racemic indoline-2-carboxylic acid methyl ester; selectively hydrolyzing (R)-form of the racemic indoline-2-carboxylic acid methyl ester in a buffer solution by use of the hydrolytic enzyme to produce (S)-indoline-2-carboxylic acid methyl ester (preferably, having a optical purity of at least 99% e.e.); and separating and recovering the (S)-indoline-2-carboxylic acid methyl ester.

The hydrolytic enzyme is selected from the group consisting of Savinase, Alcalase, Novozym 243, Everlase, Esperase, Protease 7, and Acylase. According to a second aspect of the present invention, there is provided a method for preparing (S)-indoline-2-carboxylic acid by use of a hydrolytic enzyme, having the following steps of reacting racemic indoline-2-carboxylic acid with methanol and thionyl chloride, to give racemic indoline-2-carboxylic acid methyl ester;

selectively hydrolyzing (R)-form of the racemic indoline-2-carboxylic acid methyl ester in a buffer solution by use of the hydrolytic enzyme to obtain an unhydrolyzed (S)-indoline-2-carboxylic acid methyl ester;

separating and recovering the (S)-indoline-2-carboxylic acid methyl ester; and hydrolyzing the recovered (S)-indoline-2-carboxylic acid methyl ester in an alkali aqueous solution to produce (S)-indoline-2-carboxylic acid, followed by recovering the resulting (S)-indoline-2-carboxylic acid (preferably, having a optical purity of at least 99% e.e.), The hydrolytic enzyme is selected from the group consisting of Savinase, Alcalase, Novozym 243, Everlase, Esperase, Protease 7, and Acylase.

DETAILED DESCRIPTION OF THE INVENTION

In accordance with the present invention, to produce a targeted (S)-indoline-2-carboxylic acid and (S)-indoline-2-carboxylic acid methyl ester, a reaction of racemic indoline-2-carboxylic acid with methanol and thionyl chloride is first performed.

The preparation of racemic indoline-2-carboxylic acid methyl ester is shown in the following Reaction Scheme 1:

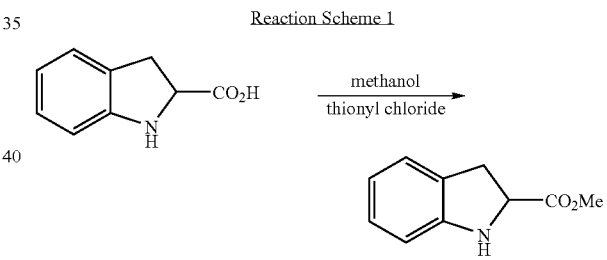

Reaction Scheme 1

Racemic indoline-2-carboxylic acid, as a starting material of Reaction Scheme 1, is dissolved in methanol and then the reaction is conducted under the slow addition of thionyl chloride to obtain racemic indoline-2-carboxylic acid methyl ester.

At this point, methanol and thionyl chloride are used in about 1 to 30 equivalents and about 1 to 2 equivalents, respectively, based on the racemic indoline-2-carboxylic acid.

Thereafter, the racemic indoline-2-carboxylic acid methyl ester is subjected to optical resolution, that is, enzymatic optical resolution, according to the following Reaction Scheme 2. As shown in Reaction Scheme 2, the racemic indoline-2-carboxylic acid methyl ester prepared by Reaction Scheme 1, which is used as a substrate, is suitably dissolved and dispersed in a buffer solution (e.g., a 100 mM sodium carbonate buffer solution), which is then added with a hydrolytic enzyme and stirred. During the hydrolysis, only a (R)-form of indoline-2-carboxylic acid methyl ester is selectively hydrolyzed by the action of hydrolytic enzyme. As a result (S)-indoline-2-carboxylic acid methyl ester remains unhydrolyzed with a high optical purity (i.e. at least 99% e.e.). The resulting (S)-indoline-2-carboxylic acid methyl ester may be separated from the (R)-indoline-2-carboxylic acid, and then recovered through any known methods in the art.

Reaction Scheme 2

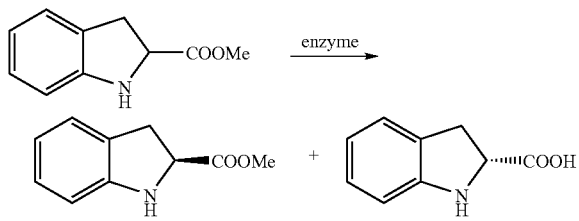

In the present invention, since the ester compound having a lower molecular weight, such as racemic indoline-2-carboxylic acid methyl ester, is utilized as the substrate of the enzyme, it increases the number of moles per unit volume in the same amount, compared to ester compounds composed of alcohol having a higher molecular weight. Thus, it is possible to develop an economical production process. Furthermore, with the aim of using the industrially available enzyme having stable titer and superior activity as the catalyst, instead of the enzyme purified from the microorganisms, the preparation of industrially available enzymes being less expensive with higher activities than those of the conventionally published industrial enzymes should be accomplished, which is essentially required for the large-scaled production.

In consideration of the above, the present inventors have applied various hydrolytic enzymes originated from microorganisms or mammals in order to search for commercially available enzymes suitable for the enantioselective hydrolysis of racemic indoline-2-carboxylic acid methyl ester. As a result the following seven enzymes can play an important role in enantioselective hydrolysis of only (R)-indoline-2-carboxylic acid methyl ester, whereby the remaining (S)-indoline-2-carboxylic acid methyl ester can be obtained as a desired product. Such industrial enzymes having the above activities are exemplified by protease families and acylase.

Examples of the protease families include Savinase (derived from *Bacillus*, Novo), Alcalase (derived from *Bacillus lichenformis*, Novo), Novozym 243 (derived from *Bacillus licheniformis*, Novo), Everlase (derived from *Bacillus*, Novo), Esperase (derived from *Bacillus*, Novo), Protease 7 (derived from *Aspergillus oryzae*, Europa), and examples of the acylase have Acylase (derived from *Penicillium*, Europa). Among the seven enzymes as described above, Savinase is preferable, since it exhibits an excellent selective hydrolysis performance for (R)-indoline-2-carboxylic acid methyl ester in a short period, to produce (S)-indoline-2-carboxylic acid methyl ester with high yield and high optical purity. Further, Savinase is very inexpensive, and thus is particularly suitable for use in a commercial process.

Savinase, which is a subtilisin-like protease having a serine group (EC 3.1.21.62), is produced through fermentation of gene-modified Alkalophilic *Bacillus* sp., and is inexpensive enough to be used at larger amounts in detergent industries (Mahmoudian M. et al., Tetrahedron: *Asymmetry*, 10, 1201, 1999). In addition, since this enzyme is purchased in the form of an aqueous solution, it can be directly applied into the reactor upon hydrolysis. Of course, the above enzyme may be taken in the form of powder or liquid, or forms immobilized on a support.

In the present invention, pH of the enzymatic reaction is preferably in the range of about 7 to 9. The too low pH results in a decreased reaction rate, whereas the excessively high pH may cause a lessened yield. Further, the temperature of the enzymatic reaction is preferably in the range of about 25 to 50° C. If the temperature is too low, the reaction rate becomes too slow. On the other hand, if the temperature is excessively high, the decrease of the optical purity is problematic.

The preferable ratio by weight of the enzyme to the substrate ranges from about 1:10 to 1:40. If the ratio is beyond the above range, the amounts of the enzyme used are too large, and thus it is difficult to maintain economic benefits, or the reaction rate may become too slow. As such, it is preferred that the substrate has a concentration of about 10-50% (w/v). If the concentration is less than 10%, the amount of the substrate is too small, thus negating economic benefits. Meanwhile, if the concentration exceeds 50%, the reaction rate becomes slow and the yield decreases. Further, the reaction time is preferable in the range of about 3 to 85 hours.

Finally, the hydrolysis for the production of optically pure (S)-indoline-2-carboxylic acid from (S)-indoline-2-carboxylic acid methyl ester obtained as above is conducted through the following Reaction Scheme 3:

Reaction Scheme 3

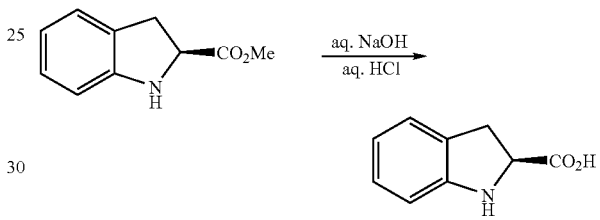

The (S)-indoline-2-carboxylic acid methyl ester prepared by Reaction Scheme 2, is hydrolyzed into (S)-indoline-2-carboxylic acid in an aqueous alkali solution (e.g., an aqueous sodium hydroxide solution), typically at room temperature without any substantial decrease of the optical purity. Then, the resulting (S)-indoline-2-carboxylic acid is recovered through the conventional method. For example, upon or after the completion of the hydrolysis, the reaction mixture is acidified with an aqueous acid solution (e.g., an aqueous hydrochloric acid solution) to maintain pH at about 5, and then extracted with an organic solvent to prepare an optically pure (S)-indoline-2-carboxylic acid.

The thus prepared (S)-indoline-2-carboxylic acid has a high optical purity of at least 99% e.e.

Having generally described this invention, a further understanding can be obtained by reference to specific examples which are provided herein for purposes of illustration only and are not intended to be limiting unless otherwise specified.

EXAMPLE 1

Preparation of Racemic Indoline-2-Carboxylic Acid Methyl Ester 25 g of indole-2-carboyxlic acid and 130 ml of methanol were placed into a 500 ml reactor equipped with a dropping funnel, after which 11.2 ml of thionyl chloride was slowly introduced through the dropping funnel thereto. After the addition of thionyl chloride, the temperature of the reaction increased to 60° C., at which stirring was additionally performed for 2 hours. The reaction product was distilled under reduced pressure to remove thionyl chloride and methanol, and then added with 130 ml of ethyl acetate, and slowly introduced with 100 ml of a saturated aqueous solution of sodium hydrogen carbonate (NaHCO₃) with stirring, and allowed to stand. The resultant reaction product was extracted twice with 130 ml of ethyl acetate by use of a separating funnel, after which an organic layer was placed in a 500 ml round bottom flask and distilled under reduced pressure to remove the solvent, thus obtaining 26.6 g of racemic indoline-2-carboxylic acid methyl ester. The reaction product was confirmed to be racemic indoline-2-carboxylic acid methyl ester by means of nuclear magnetic resonance analysis. The NMR result was as follows:

1H NMR (200 MHz, CDCl₃) δ 3.38 (dd, 2H), 3.77 (s, 3H), 4.40 (dd, 1H), 6.76 (t 2H), 7.07 (t, 2H)

EXAMPLE 2

Optical Resolution of Racemic Ester Using Industrial Hydrolytic Enzyme 80 ml of a 100 mM carbonate buffer solution (pH 8.0) was added with 20 g of the racemic indoline-2-carboyxlic acid methyl ester prepared in Example 1, and controlled in pH 8.0, and then further quantitatively added with 1 g of Savinase (Novo) for the enzymatic resolution. The reaction was carried out at 35° C. As such, the pH was maintained in the range of 7.8 to 8.2, using a 5N sodium hydroxide solution. Thereafter, at each regular interval, 0.1 ml of the resultant reaction product was mixed well with 0.1 ml of the saturated aqueous solution of sodium hydrogen carbonate, and then extracted with 0.5 ml of ethyl acetate, and thus analyzed by use of a gas chromatography.

As for the gas chromatographic conditions, a silica-filled capillary column (Beta-DEX 120, 30m×0.25 mm×0.25m, Supelco) was allowed to stand at 160° C. for 1 min, and increased to 180° C. at a rate of 1° C./min, and then allowed to stand for 5 min. Helium as a carrier gas was applied at 1 ml/min, and detection was performed 250° C. by use of a flame ionization detector (FID). In practice, since (R)-indoline-2-carboxylic acid methyl ester was detected at 17.0 min, while (S)-indoline-2-carboxylic acid methyl ester was detected at 17.4 min. The two isomers were easily discriminated.

Analytic results were represented by yield [%] and optical purity [% e.e.], and the yield and optical purity of (S)-ester was calculated according to Equations 1 and 2, respectively:

$$\text{Yield (\%)} = \frac{\text{weight (g) of (S)-ester compound after reaction}}{\text{weight (g) of racemic ester compound before reaction}} \times 100 \qquad \text{Equation 1}$$

$$\text{Optical Purity (\% }e.e\text{)} = \frac{[(S)\text{-ester}] - [(R)\text{-ester}]}{[(S)\text{-ester}] + [(R)\text{-ester}]} \times 100 \qquad \text{Equation 2}$$

The optical purity (% e.e.) of (S)-indoline-2-carboxylic acid methyl ester was measured according to the reaction time. The results are shown in Table 1, below.

TABLE 1

| Optical Purity (% e.e.) of (S)-Indoline-2-Carboxylic Acid Methyl Ester according to Reaction Time | |
| --- | --- |
| Reaction Time (hr) | Optical Purity (% e.e.) |
| 1 | 62.7 |
| 2 | 87.0 |

TABLE 1-continued

| Optical Purity (% e.e.) of (S)-Indoline-2-Carboxylic Acid Methyl Ester according to Reaction Time | |
| --- | --- |
| Reaction Time (hr) | Optical Purity (% e.e.) |
| 3 | 95.5 |
| 4 | 97.9 |
| 5 | 99.3 |

After the reaction occurred for five hours, the reaction was stopped when the optical purity of (S)-indoline-2-carboxylic acid methyl ester reached 99% e.e. or more. The reaction solution was transferred to the separating funnel, and then extracted three times with 80 ml of ethyl acetate. The organic solvent layer was separated and distilled under reduced pressure to remove the solvent. As a result, 9.38 g of (S)-indoline-2-carboxylic acid methyl ester was attained, after which an analysis with gas chromatography was performed. As such, (S)-indoline-2-carboxylic acid methyl ester had the yield of 47.0% and the optical purity of 99.3% e.e.

EXAMPLE 3

Preparation of (S)-indoline-2-Carboxylic Acid Through Hydrolysis

Into a 250 ml reactor equipped with a pH meter, 8.1 g of (S)-indoline-2-carboxylic acid methyl ester prepared in Example 2 and 50 ml of 1N aqueous sodium hydroxide solution were placed and strongly stirred at room temperature. Whether (S)-indoline-2-carboxylic acid methyl ester was converted to (S)-indoline-2-carboxylic acid was confirmed. Then, while the temperature of the reactor was maintained at 20° C. or less, 1N aqueous hydrochloric acid solution was slowly added to the reactor to control pH 5. The resultant reaction product was extracted three times with 50 ml of ethyl acetate by use of the separating funnel, and the organic layer was placed into a round bottom flask. The solvent in the organic layer was removed through distillation under reduced pressure, to give 7.0 g of (S)-indoline-2-carboxylic acid. The thus prepared (S)-indoline-2-carboxylic acid was analyzed for optical purity by means of liquid chromatography.

As for the liquid chromatographic conditions, a chiralpak AD column (Daicel) composed of amylose derivatives was used, and hexane, isopropanol and trifluoroacetic acid having a ratio of 95:5:0.1 as an eluent were applied at 1 ml/min. The reaction product was detected at UV 220 nm. As the reactants of the above reaction, (S)-indoline-2-carboxylic acid methyl ester was detected at 11.9 min, while (R)-indoline-2-carboxylic acid methyl ester was detected at 12.4 min. Further, as the hydrolyzed products, (S)-indoline-2-carboxylic acid was at 23.8 min, while (R)-indoline-2-carboxylic acid at 32.0 min.

Analytic results were represented by yield [%] and optical purity [% e.e.], in which the yield of (S)-ester was calculated according to Equation 3, and the optical purity thereof accorded to Equation 2:

$$\text{Yield (\%)} = \frac{\text{number of moles (mol) of (S)-carboxylic acid after reaction}}{\text{number of moles (mol) of (S)-ester compound before reaction}} \times 100 \qquad \text{Equation 3}$$

(S)-indoline-2-carboxylic acid produced by the hydrolysis was 94.5% in the yield and 99.3% e.e. in the optical purity.

EXAMPLES 4-10

The present examples were performed while the amounts of the substrate and the enzyme, the reaction temperature, and the volume of the buffer solution were maintained in the same as the reaction conditions of Example 2, with the exception that pH of the buffer solution was variously changed to 6.5, 7.0, 7.5, 8.0, 8.5, 9.0 and 10.0. The resultant reaction product was analyzed every hour, and the reaction was stopped when the optical purity of (S)-indoline-2-carboxylic acid methyl ester reached about 99% e.e. The reaction product was recovered as in Example 2 and analyzed. The results are given in Table 2, below.

TABLE 2

Reaction Time, Yield (%) and Optical Purity (% e.e.) of (S)-Indoline-2-Carboxylic Acid Methyl Ester according to pH of Buffer Solution

| Ex. No. | pH | Time (hr) | Yield (%) | Optical Purity (% e.e.) |
|---|---|---|---|---|
| 4 | 6.5 | 80 | 55.0 | 96.2 |
| 5 | 7.0 | 33 | 48.2 | 99.1 |
| 6 | 7.5 | 11 | 47.3 | 99.5 |
| 7 | 8.0 | 5 | 47.0 | 99.3 |
| 8 | 8.5 | 3 | 45.6 | 99.0 |
| 9 | 9.0 | 2 | 43.6 | 98.9 |
| 10 | 10.0 | 2 | 6.3 | 98.8 |

EXAMPLES 11-17

The present examples were performed while the amounts of the substrate and the enzyme, and the pH and volume of the buffer solution were maintained in the same as the reaction conditions of Example 2, with the exception that the reaction temperature was variously changed to 25, 30, 35, 40, 45, 50 and 60° C. The resultant reaction product was analyzed every hour, and the reaction was stopped when the optical purity of (S)-indoline-2-carboxylic acid methyl ester reached about 99% e.e. The reaction product was recovered as in Example 2 and analyzed. The results are shown in Table 3, below.

TABLE 3

Reaction Time, Yield (%) and Optical Purity (% e.e.) of (S)-Indoline-2-Carboxylic Acid Methyl Ester according to Reaction Temperature (° C.)

| Ex. no. | Temp. (° C.) | Time (hr) | Yield (%) | Optical Purity (% e.e.) |
|---|---|---|---|---|
| 11 | 25 | 7 | 46.9 | 99.2 |
| 12 | 30 | 7 | 46.6 | 99.4 |
| 13 | 35 | 5 | 47.0 | 99.3 |
| 14 | 40 | 4 | 46.8 | 99.0 |
| 15 | 45 | 4 | 44.5 | 99.5 |
| 16 | 50 | 3 | 44.7 | 99.1 |
| 17 | 60 | 5 | 55.1 | 77.8 |

EXAMPLES 18-22

The present examples were performed while the pH and volume of the buffer solution, and the reaction temperature were maintained in the same as the reaction conditions of Example 2, with the exception that the amount of the substrate was variously changed to 10, 20, 30, 40 and 50 g at the ratio of substrate/enzyme set to 20. The resultant reaction product was analyzed every hour, and the reaction was stopped when the optical purity of (S)-indoline-2-carboxylic acid methyl ester reached about 99% e.e. The reaction product was recovered as in Example 2 and analyzed. The results are presented in Table 4, below.

TABLE 4

Reaction Time, Yield (%) and Optical Purity (% e.e.) of (S)-Indoline-2-Carboxylic Acid Methyl Ester according to Amount of Substrate (g)

| Ex. No. | Substrate (g) | Enzyme (g) | Time (hr) | Yield (%) | Optical Purity (% e.e.) |
|---|---|---|---|---|---|
| 18 | 10 | 0.5 | 3 | 44.0 | 99.5 |
| 19 | 20 | 1 | 5 | 47.0 | 99.3 |
| 20 | 30 | 1.5 | 9 | 47.1 | 99.0 |
| 21 | 40 | 2 | 14 | 49.1 | 99.3 |
| 22 | 50 | 2.5 | 44 | 27.6 | 98.9 |

The present examples were performed while the amount of the substrate, the pH and volume of the buffer solution, and the reaction temperature were maintained in the same as the reaction conditions of Example 2, with the exception that the ratio of substrate/enzyme was variously changed to 10, 20, 30 and 40. The resultant reaction product was analyzed every hour, and the reaction was stopped when the optical purity of (S)-indoline-2-carboxylic acid methyl ester reached about 99% e.e. The reaction product was recovered as in Example 2 and analyzed. The results are shown in Table 5, below.

TABLE 5

Reaction Time, Yield (%) and Optical Purity (% e.e.) of (S)-Indoline-2-Carboxylic Acid Methyl Ester according to Ratio of Substrate/Enzyme

| Ex. No. | Substrate/ Enzyme | Enzyme (g) | Time (hr) | Yield (%) | Optical Purity (% e.e.) |
|---|---|---|---|---|---|
| 23 | 10 | 2 | 3 | 44.0 | 99.7 |
| 24 | 20 | 1 | 5 | 47.0 | 99.3 |
| 25 | 30 | 0.67 | 7 | 44.7 | 99.0 |
| 26 | 40 | 0.5 | 9 | 43.6 | 99.6 |

EXAMPLES 27-33

The present examples were performed while the pH and volume of the buffer solution, the amount of the substrate, and the reaction temperature were maintained in the same as the reaction conditions of Example 2, with the exception that the amount of the enzyme was changed to 4 g, and as the industrial enzyme was used Savinase, Alcalase, Novozym 243, Everlase, Esperase, Protease 7 and Acylase. The resultant reaction product was analyzed every hour, and the reaction was stopped when the optical purity of (S)-indoline-2-carboxylic acid methyl ester reached about 99% e.e. The reaction product was recovered as in Example 2 and analyzed. The results are given in Table 6, below.

TABLE 6

Reaction Time, Yield (%) and Optical Purity (% e.e.) of (S)-Indoline-2-Carboxylic Acid Methyl Ester according to Enzyme

| Ex. No. | Enzyme | Time (hr) | Yield (%) | Optical Purity (% e.e.) |
|---|---|---|---|---|
| 27 | Savinase | 1 | 43.8 | 99.5 |
| 28 | Alcalase | 2 | 31.4 | 99.6 |

TABLE 6-continued

Reaction Time, Yield (%) and Optical Purity
(% e.e.) of (S)-Indoline-2-Carboxylic Acid
Methyl Ester according to Enzyme

| Ex. No. | Enzyme | Time (hr) | Yield (%) | Optical Purity (% e.e.) |
|---|---|---|---|---|
| 29 | Novozym 243 | 3 | 36.8 | 99.7 |
| 30 | Everlase | 3 | 42.9 | 99.5 |
| 31 | Esperase | 5 | 40.2 | 99.3 |
| 32 | Protease 7 | 7 | 35.5 | 98.5 |
| 33 | Acylase | 9 | 30.2 | 99.0 |

As described hereinbefore, the present invention provides a method for preparing (S)-indoline-2-carboxylic acid and methyl ester thereof having a very high optical purity of at least 99% e.e., by using a commercially available hydrolytic enzyme, which is advantageous in terms of a simplified preparation process, thus generating economic benefits.

Although the preferred embodiments of the present invention have been disclosed for illustrative purposes, those skilled in the art will appreciate that various modifications, additions and substitutions are possible. Therefore, it is to be understood that within the scope of the appended claims, the invention may be practiced otherwise than as specifically described.

The invention claimed is:

1. A method for preparing (S)-indoline-2-carboxylic acid methyl ester by use of a hydrolytic enzyme, comprising the following steps:
   reacting racemic indoline-2-carboxylic acid with methanol and thionyl chloride, to give racemic indoline-2-carboxylic acid methyl ester;
   selectively hydrolyzing (R)-form of the racemic indoline-2-carboxylic acid methyl ester in a buffer solution by use of the hydrolytic enzyme to produce (S)-indoline-2-carboxylic acid methyl ester; and
   separating and recovering the (S)-indoline-2-carboxylic acid methyl ester, wherein said hydrolytic enzyme is selected from the group consisting of Savinase, Alcalase, Novozym 243, Everlase, Esperase, Protease 7, and Acylase.

2. The method as defined in claim 1, wherein the buffer solution is an aqueous sodium carbonate solution, and is maintained in pH 7 to 9.

3. The method as defined in claim 1, wherein the selective hydrolyzing step is performed at 25 to 50° C. for 3 to 85 hours.

4. The method as defined in claim 1, wherein a ratio by weight of the hydrolytic enzyme to the racemic indoline-2-carboxylic acid methyl ester is in a range of 1:10 to 1:40.

5. The method as defined in claim 1, wherein the concentration of the racemic indoline-2-carboxylic acid methyl ester ranges from 10 to 50% (w/w) in the selective hydrolyzing step.

6. The method as defined in claim 1, wherein the hydrolytic enzyme takes the form of powder or liquid, or forms immobilized on a support.

7. The method as defined in claim 1, wherein the recovered (S)-indoline-2-carboxylic acid methyl ester has an optical purity of at least 99% e.e.

8. A method for preparing (S)-indoline-2-carboxylic acid by use of a hydrolytic enzyme, comprising the following steps:
   reacting racemic indoline-2-carboxylic acid with methanol and thionyl chloride, to give racemic indoline-2-carboxylic acid methyl ester;
   selectively hydrolyzing (R)-form of the racemic indoline-2-carboxylic acid methyl ester in a buffer solution by use of the hydrolytic enzyme to obtain an unhydrolyzed (S)-indoline-2-carboxylic acid methyl ester;
   separating and recovering the (S)-indoline-2-carboxylic acid methyl ester; and
   hydrolyzing the recovered (S)-indoline-2-carboxylic acid methyl ester in an alkali aqueous solution to produce (S)-indoline-2-carboxylic acid, followed by recovering the resulting (S)-indoline-2-carboxylic acid,
   wherein, said hydrolytic enzyme is selected from the group consisting of Savinase, Alcalase, Nvozym 243, Everlase, Esperase, Protease 7, and Acylase.

9. The method as defined in claim 8, wherein the buffer solution is an aqueous sodium carbonate solution, and is maintained in pH 7 to 9.

10. The method as defined in claim 8, wherein the selective hydrolyzing step is performed at 25 to 50° C. for 3 to 85 hours.

11. The method as defined in claim 8, wherein a ratio by weight of the hydrolytic enzyme to the racemic indoline-2-carboxylic acid methyl ester is in a range of 1:10 to 1:40.

12. The method as defined in claim 8, wherein the concentration of the racemic indoline-2-carboxylic acid methyl ester ranges from 10 to 50% (w/w) in the selective hydrolyzing step.

13. The method as defined in claim 8, wherein the hydrolytic enzyme takes the form of powder or liquid or forms immobilized on a support.

14. The method as defined in claim 8, wherein the recovered (S)-indoline-2-carboxylic acid has an optical purity of at least 99% e.e.

* * * * *

UNITED STATES PATENT AND TRADEMARK OFFICE
CERTIFICATE OF CORRECTION

| | | |
|---|---|---|
| PATENT NO. | : 7,405,070 B2 | Page 1 of 1 |
| APPLICATION NO. | : 10/596068 | |
| DATED | : July 29, 2008 | |
| INVENTOR(S) | : Nahm Ryune Cho et al. | |

It is certified that error appears in the above-identified patent and that said Letters Patent is hereby corrected as shown below:

Title page item (73),
Please remove "SK Corporation" and insert --SK Holdings Co., Ltd.--

Signed and Sealed this

Fifth Day of October, 2010

David J. Kappos
*Director of the United States Patent and Trademark Office*